(12) United States Patent
Cai et al.

(10) Patent No.: US 10,039,675 B1
(45) Date of Patent: Aug. 7, 2018

(54) RETAINING DEVICE FOR RETAINING SMALL-SIZED DETECTIVE SENSOR

(71) Applicant: Dongguan Southstar Electronics Limited, Dongguan (CN)

(72) Inventors: Fangyi Cai, Dongguan (CN); Jun Yi, Dongguan (CN); Minghui Du, Dongguan (CN); Hongjun Yan, Dongguan (CN)

(73) Assignee: DONGGUAN SOUTHSTAR ELECTRONICS LIMITED, Dongguan, Guangdong (CN)

( * ) Notice: Subject to any disclaimer, the term of this patent is extended or adjusted under 35 U.S.C. 154(b) by 0 days.

(21) Appl. No.: 15/498,431

(22) Filed: Apr. 26, 2017

(51) Int. Cl.
*A61F 13/42* (2006.01)
*A44B 18/00* (2006.01)
*A45F 5/02* (2006.01)

(52) U.S. Cl.
CPC .......... *A61F 13/42* (2013.01); *A44B 18/0069* (2013.01); *A45F 5/02* (2013.01); *Y10T 24/27* (2015.01)

(58) Field of Classification Search
CPC ...... A61F 13/42; Y10T 24/27; Y10T 24/2708; A44B 18/0069
See application file for complete search history.

(56) References Cited

U.S. PATENT DOCUMENTS

| 3,812,851 | A | * | 5/1974 | Rodriguez | ............... | A61M 5/52 128/877 |
| 4,898,587 | A | * | 2/1990 | Mera | ..................... | A61M 25/02 128/DIG. 26 |
| 5,413,562 | A | * | 5/1995 | Swauger | ............... | A61M 25/02 128/DIG. 26 |
| 2005/0060917 | A1 | * | 3/2005 | Kenson | ................ | A43B 3/0078 36/136 |
| 2010/0004612 | A1 | * | 1/2010 | Thevenin | ................ | A61F 13/42 604/361 |

* cited by examiner

*Primary Examiner* — Robert Sandy
*Assistant Examiner* — Michael S Lee
(74) *Attorney, Agent, or Firm* — Leong C. Lei

(57) ABSTRACT

A retaining device for retaining a small-sized detective sensor includes a flexible rubber body. The flexible rubber body includes a first retaining portion, a first connecting portion, a main body portion, a second connecting portion, and a second retaining portion which are connected in sequence. An inner side of the first retaining portion and an inner side of the second retaining portion are provided with primary Velcro retaining straps. An inner side of the main body portion is formed with a recess for installing the small-sized detective sensor.

9 Claims, 3 Drawing Sheets

RETAINING DEVICE FOR RETAINING SMALL-SIZED DETECTIVE SENSOR

FIELD OF THE INVENTION

The present invention relates to a retaining device, and more particularly to a retaining device for retaining a small-sized detective sensor.

BACKGROUND OF THE INVENTION

These days, there are many IoT (Internet of Things) products on the market, such as human body surface temperature and humidity sensors, 3 g gravity sensors, and other devices for urine detection, motion mass detection, and so on. However, most of these sensors have the common feature that they are small in size and that they must be closely attached to the clothing on the human body when in use. Conventional retaining devices are unable to retain these small-sized detective sensors, so that the accuracy and reliability of the collected data is poor. Accordingly, the inventor of the present invention has devoted himself based on his many years of practical experiences to solve these problems.

SUMMARY OF THE INVENTION

In view of the shortcomings of the prior art, the primary object of the present invention is to provide a retaining device for retaining a small-sized detective sensor.

In order to achieve the aforesaid object, the retaining device for retaining a small-sized detective sensor of the present invention comprises a flexible rubber body. The flexible rubber body includes a first retaining portion, a first connecting portion, a main body portion, a second connecting portion, and a second retaining portion which are connected in sequence. An inner side of the first retaining portion and an inner side of the second retaining portion are provided with primary Velcro retaining straps. An inner side of the main body portion is formed with a recess for installing the small-sized detective sensor.

Preferably, the first retaining portion, the first connecting portion, the main body portion, the second connecting portion, and the second retaining portion are integrally formed and connected in sequence.

Preferably, the flexible rubber body is made of a silicone material.

Preferably, each of the primary Velcro retaining straps is a Velcro strap having dense and small hooks and loops.

Preferably, an outer side of the main body portion has a press portion.

Preferably, the first connecting portion and the second connecting portion are provided with a plurality of perforations.

Preferably, the inner side of the main body portion is provided with an auxiliary Velcro retaining strap, and the auxiliary Velcro retaining strap is located beside the recess.

Preferably, the auxiliary Velcro retaining strap is a Velcro strap having dense and small hooks and loops.

Preferably, the number of the auxiliary Velcro retaining strap is two, and the two auxiliary Velcro retaining straps are symmetrically disposed at two sides of the recess.

Preferably, the auxiliary Velcro retaining strap has an arc shape.

Compare to the prior art, the present invention has obvious advantages and beneficial effects. The flexible rubber body is provided with the recess for installing the small-sized detective sensor, the primary Velcro retaining straps, and the auxiliary Velcro retaining straps, so that the small-sized detective sensor is firmly fixed and attached to the outer surface of the paper diaper. The small-sized detective sensor won't be detached from the paper diaper due to a large swing, thereby effectively enhancing the accuracy and reliability of the small-sized detective sensor.

DETAILED DESCRIPTION OF THE PREFERRED EMBODIMENTS

Embodiments of the present invention will now be described, by way of example only, with reference to the accompanying drawings.

Figure 1:
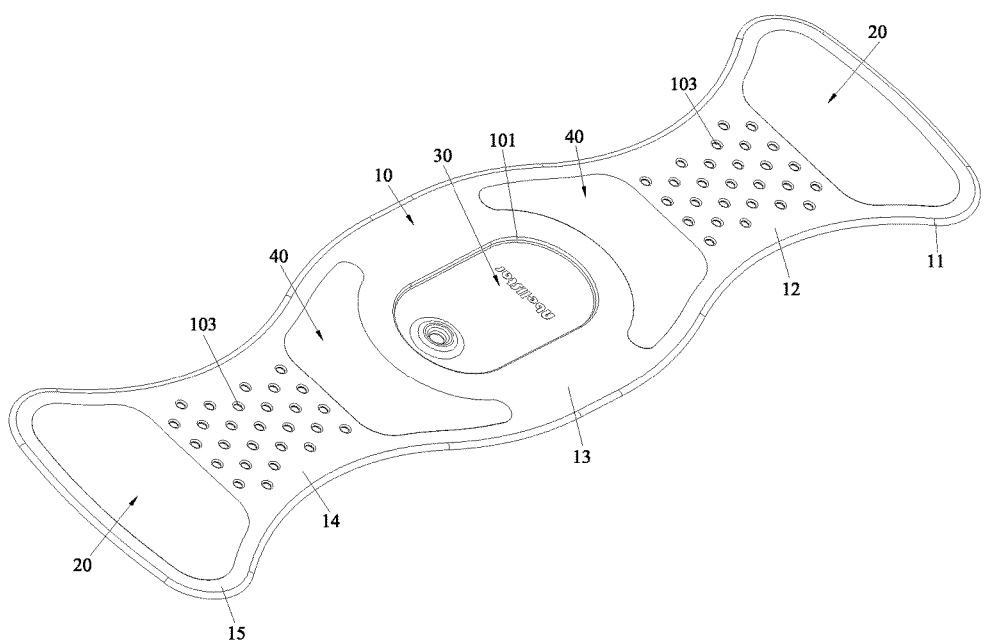
FIG. 1 is a perspective view in accordance with a preferred embodiment of the present invention.
Figure 2:
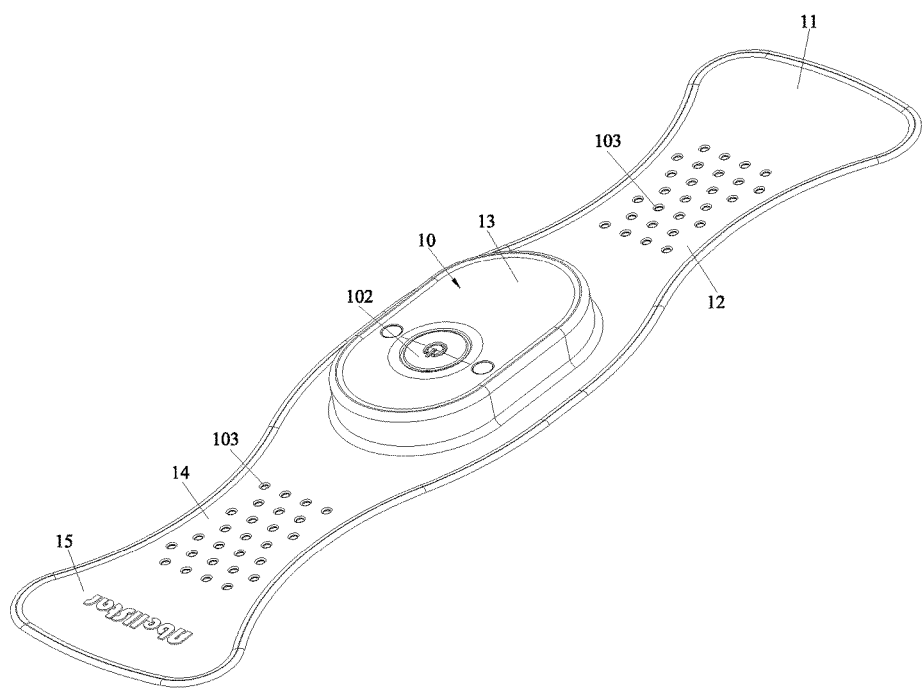
FIG. 2 is another perspective view in accordance with the preferred embodiment of the present invention.
Figure 3:
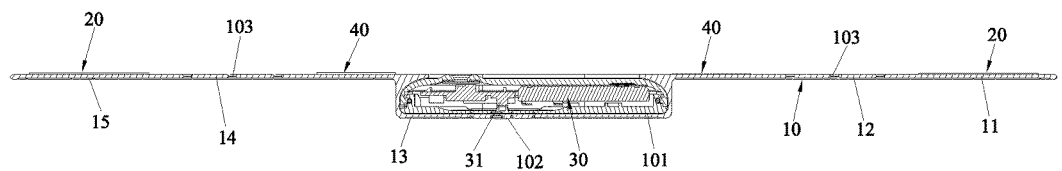
FIG. 3 is a sectional view in accordance with the preferred embodiment of the present invention.

As shown in FIG. 1 to FIG. 3, a preferred embodiment of the present invention comprises a flexible rubber body 10. The flexible rubber body 10 includes a first retaining portion 11, a first connecting portion 12, a main body portion 13, a second connecting portion 14, and a second retaining portion 15 which are integrally formed and connected in sequence. An inner side of the first retaining portion 11 and an inner side of the second retaining portion 15 are provided with primary Velcro retaining straps 20. An inner side of the main body portion 13 is formed with a recess 101 for installing a small-sized detective sensor 30. The inner side of the main body portion 13 is provided with an auxiliary Velcro retaining strap 40. The auxiliary Velcro retaining strap 40 is located beside the recess 101.

In this embodiment, the flexible rubber body 10 is made of a silicone material. An outer side of the main body portion 13 has a press portion 102 for the user to press a control button 31 of the small-sized detective sensor 30. The first connecting portion 12 and the second connecting portion 14 are provided with a plurality of perforations 103 to enhance the air permeability and also to enhance the elastic force of the first connecting portion 12 and the second connecting portion 14. The width of the first connecting portion 12 and the second connecting portion 14 is less than the width of the first retaining portion 11, the main body portion 13, and the second retaining portion 15.

The primary Velcro retaining strap 20 is a Velcro strap having dense and small hooks and loops. The auxiliary Velcro retaining strap 40 is also a Velcro strap having dense and small hooks and loops. In this embodiment, the number of the auxiliary Velcro retaining strap 40 is two, and the two auxiliary Velcro retaining straps 40 are symmetrically disposed at two sides of the recess 101. The auxiliary Velcro retaining strap 40 has an arc shape.

The small-sized detective sensor 30 may be used for urine detection, rapid eye movement sleep detection, and the like. The product is mainly composed of a detection module, such as a temperature and humidity sensor, and a Bluetooth or a wireless communication module. The specific structure and working principle are prior art. The specific structure and working principle of the detective sensor 30 are not described hereinafter.

The details of the use of this embodiment are as follows:

In use, the small-sized detective sensor 30 is mounted in the recess 101, and then the small-sized detective sensor 30 is placed at a detection position to get contact with the outer surface of a paper diaper. The auxiliary Velcro retaining straps 40 are attached to the outer surface of the paper diaper, so that the small-sized detective sensor 30 is held in close contact with the paper diaper. After that, the first retaining portion 11 and the second retaining portion 15 are respectively tensioned toward both sides, and then the two primary Velcro retaining straps 20 are respectively adhered to the two sides of the outer surface of the paper diaper. In addition, the small-sized detective sensor 30 is firmly fixed and adhered to the outer surface of the paper diaper. The small-sized detective sensor 30 won't be detached from the paper diaper due to a large swing, thereby effectively enhancing the accuracy and reliability of the small-sized detective sensor 30.

The feature of the present invention is that the flexible rubber body is provided with the recess for installing the small-sized detective sensor, the primary Velcro retaining straps, and the auxiliary Velcro retaining straps, so that the small-sized detective sensor is firmly fixed and attached to the outer surface of the paper diaper. The small-sized detective sensor won't be detached from the paper diaper due to a large swing, thereby effectively enhancing the accuracy and reliability of the small-sized detective sensor.

Although particular embodiments of the present invention have been described in detail for purposes of illustration, various modifications and enhancements may be made without departing from the spirit and scope of the present invention. Accordingly, the present invention is not to be limited except as by the appended claims.

What is claimed is:

1. A retaining device for retaining a small-sized detective sensor, comprising a flexible rubber body; the flexible rubber body including a first retaining portion, a first connecting portion, a main body portion, a second connecting portion, and a second retaining portion which are connected in sequence, an inner side of the first retaining portion and an inner side of the second retaining portion being provided with primary retaining straps, an inner side of the main body portion being formed with a recess for installing the small-sized detective sensor;

wherein the recess formed in the inner side of the main body portion is delimited by a continuous, non-interrupted circumferential sidewall that circumferentially encloses the small-sized detective sensor installed in the recess;

wherein each of the primary retaining straps that are provided on the inner sides of the first and second retaining portions comprise dense and small hooks adapted to commonly engage with an external surface so as to attach the small-sized detective sensor to the external surface.

2. The retaining device as claimed in claim 1, wherein the first retaining portion, the first connecting portion, the main body portion, the second connecting portion, and the second retaining portion are integrally formed and connected in sequence.

3. The retaining device as claimed in claim 1, wherein the flexible rubber body is made of a silicone material.

4. The retaining device as claimed in claim 1, wherein an outer side of the main body portion has a press portion that is in physical engagement with a control button of the small-sized detective sensor.

5. The retaining device as claimed in claim 1, wherein the first connecting portion and the second connecting portion are provided with a plurality of perforations.

6. The retaining device as claimed in claim 1, wherein the inner side of the main body portion is provided with an auxiliary retaining strap, and the auxiliary retaining strap is located beside the recess.

7. The retaining device as claimed in claim 6, wherein the auxiliary retaining strap having dense and small hooks.

8. The retaining device as claimed in claim 6, wherein the number of the auxiliary retaining strap is two, and the two auxiliary retaining straps are symmetrically disposed at two sides of the recess.

9. The retaining device as claimed in claim 6, wherein the auxiliary retaining strap has an arc shape.

\* \* \* \* \*